United States Patent
Sakurada et al.

[11] Patent Number: 6,051,685
[45] Date of Patent: Apr. 18, 2000

[54] PEPTIDE DERIVATIVES

[75] Inventors: Shinobu Sakurada, Sendai; Kimie Murayama, Niiza; Masaharu Nakano, Takaoka; Kazuya Hongo, Takaoka; Satoko Takeshima, Takaoka; Nobuhiro Take, Takaoka, all of Japan

[73] Assignee: Daiichi Pharmaceuticals Co., Ltd., Japan

[21] Appl. No.: 09/145,648

[22] Filed: Sep. 2, 1998

Related U.S. Application Data

[63] Continuation-in-part of application No. 08/704,723, Nov. 13, 1996, abandoned.

[30] Foreign Application Priority Data

Mar. 11, 1994 [JP] Japan ........................ 6-40989
Mar. 9, 1995 [WO] WIPO ................. PCT/JP95/00389

[51] Int. Cl.[7] .................................................. A61K 38/06
[52] U.S. Cl. .................... 530/331; 530/317; 530/330; 930/21
[58] Field of Search .................. 530/317, 330, 530/331; 930/21

[56] References Cited

FOREIGN PATENT DOCUMENTS 2166139  4/1986  United Kingdom .

OTHER PUBLICATIONS

P. Paakkari, et al., Journal of Pharmacology & Experimental Therapeutics, "Dermorphin Analog Try–D–Arg[2]–Phe–Sarocosine–Induced Opioid Analgesia and Respiratory Stimulation: The Role of $Mu_1$–Receptors?" vol. 266, No. 2, 1993, pp. 544–550.

Dialog File 351 (World Patent Index) print out for JP–61–103898 published May 22, 1986.

Marastoni et al., J. Med. Chem. vol. 30, pp. 1538–1542, Sep. 1987.

Suzuki et al., Chem. Pharm. Bull., vol. 36(12) pp. 4834–4840, Dec. 1988.

Spatola, "Chem. & Biochem. of Amino Acids, Peptides & Proteins", vol. 7 (Weinstein, Ed.) pp. 277–280, 1983.

*Primary Examiner*—Bennett Celsa
*Attorney, Agent, or Firm*—Griffin, Butler, Whisenhunt & Szipl, LLP

[57] ABSTRACT

A peptide derivative having analgesic activity represented by the following Formula I:

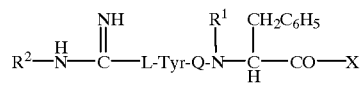

wherein Q represents D-Arg or L-Arg; and X represents for example $NR^6$—$CHR^7R^8$. Typical compounds include $H_2NC(NH)$-Tyr-D-Arg-Phe-$NHCH_2CH_2COOH$ and $H_2NC(NH)$-Tyr-D-Arg-Phe-$NHCH_2CH_2CONH_2$.

1 Claim, No Drawings

PEPTIDE DERIVATIVES

The present application is a Continuation-in-Part Application of U.S. patent application Ser. No. 08/704,723, filed Nov. 13, 1996 (now abandoned), which is an application under 35 U.S.C. 371, based on PCT/JP95/00389, filed Mar. 9, 1995, which claims priority of Japanese Patent Application No. Hei 6-40989, filed Mar. 11, 1994. The entirety of the respective disclosures of all of the above applications are specifically incorporated by reference herein.

FIELD OF THE INVENTION

The present invention relates to peptide derivatives exhibiting pharmaceutical activities such as analgesic activity through actions on opioid receptors and the like.

BACKGROUND ART

The existence of opioid receptors to which opioids such as morphine bind was verified in the early 1970's. At present, opioid receptors are mainly classified into three types, i.e., $\mu$, $\delta$ and $\kappa$. Morphine mostly acts on the $\mu$ acceptor as an agonist and exhibits pharmaceutical activities such as analgesic activity, enterokinetic inhibition, and respiratory inhibition.

Since 1975, several endogenous morphine-like substances that bind to the opioid receptors have been successively discovered. All of these substances found to date are peptide compounds and are collectively referred to as opioid peptides. The pharmaceutical activities of the opioid peptides are believed to be basically the same as those of morphine. They are expected to be safer drugs than morphine since they naturally exist in human tissues or organs. However, natural opioid peptides have problems from the pharmacokinetical standpoint, and they have not been used as clinical medicaments.

In the 1980's, Dermorphin that contains D-alanine residue was isolated from the cutises of frogs. It was found that Delmorfine has an about 1,000-fold higher analgesic effect than morphine with intraventricular administration and is relatively stable in living bodies. Since then, synthetic opioid peptides containing D-amino acid residues have been prepared. In particular, synthetic opioid peptides with high K acceptor selectivity are seen as hopeful non-narcotic analgesics and clinical trials have begun. However, the probability of their success as clinical medicaments is doubtful from the viewpoints of efficacy, possible side effects due to properties as K agonists, and commercial practicability.

Furthermore, it is impossible to use these synthesized opioid peptides as orally available medicaments, and accordingly, they can not be substitutive drugs for MS contin, e.g., which is an orally available controlled release preparation comprising morphine sulfate that has been widely used recently as a medicament for the treatment of cancerous pain. Daily doses of MS contin may occasionally be increased up to gram order, which sometimes leads to difficulty in oral administration. In some cases, its administration cannot be continued because of side effects such as pruritus due to its activity on the release of histamine. Therefore, substitute medicaments are desired which have higher safety and efficacy than morphine.

DISCLOSURE OF THE INVENTION

In order to achieve the aforementioned objects, the inventors of the present invention conducted various studies aimed at providing opioid peptide derivatives having excellent analgesic activity and oral absorbability. As a result, they found that oligopeptide derivatives and their salts having a basic structure of L-Tyr-(L or D)-Arg-Phe and an amidino group at their N-terminals have the desired properties. The present invention was achieved on the basis of these findings.

The peptide derivatives of the present invention can be represented by the following Formula I.

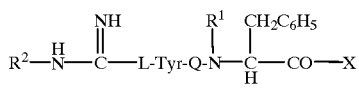

BEST MODE FOR CARRYING OUT THE INVENTION

The substituents in the above formula will be explained below. Q represents D-Arg (D-arginine residue) or L-Arg (L-arginine residue) and $R^1$ represents a hydrogen atom or a $C_{1-6}$ (1 to 6 carbon atoms) alkyl group. Compounds wherein Q is D-Arg and $R^1$ is a hydrogen atom are preferred. $R^2$ represents a hydrogen atom, a $C_{1-6}$ alkyl group, an aryl group, a $C_{1-6}$ alkanoyl group, or an arylcarbonyl group. For example, aryl groups such as substituted or non-substituted phenyl groups, preferably a non-substituted phenyl group; alkanoyl groups such as an acetyl group or a propanoyl group; and aryl carbonyl groups such as a benzoyl group may be used as the aryl group, alkanoyl group, and arylcarbonyl group.

X represents any one of $-OR^3$, $-NR^4R^5$, and $-NR^6-CR^7R^8R^9$. $R^3$ represents a hydrogen atom or a $C_{1-6}$ alkyl group, and $R^4$ represents a hydrogen atom or a $C_{1-6}$ alkyl group. $R^5$ represents a $C_{1-6}$ hydroxyalkyl group or a sulfonic acid-substituted $C_{1-6}$ alkyl group. Although the hydroxyl group or sulfonic acid group may substitute on any position of the alkyl group, terminally-substituted alkyl groups are preferred. $R^4$ and $R^5$ may combine together with the nitrogen atom to which $R^4$ and $R^5$ bind to form a 5 or 6-membered nitrogen-containing saturated heterocyclic group. The heterocyclic group may contain two or more nitrogen atoms. For example, 1-piperazinyl group, 1-pyrrolidinyl group, or 1-piperidinyl group may be used as $-NR^4R^5$.

Where X is $-NR^6-CR^7R^8R^9$, $R^6$ represents a hydrogen atom, a $C_{1-6}$ alkyl group, or a $C_{1-6}$ alkyl group substituted with an aryl group such as a phenyl group (aralkyl group). An example of the aralkyl group is a benzyl group. $R^7$ represents a hydrogen atom; carboxyl group; a carbonyl group substituted with a $C_{1-6}$ alkoxy group such as methoxy carbonyl or ethoxy carbonyl group; a substituted or non-substituted carbamoyl group; a $C_{1-6}$ alkyl group substituted with a carboxyl group; a $C_{1-6}$ alkyl group substituted with a substituted or non-substituted carbamoyl group; or a $C_{1-6}$ alkyl group having a carbonyl group substituted with a $C_{1-6}$ alkoxy group.

$R^8$ represents a hydrogen atom; a $C_{1-6}$ alkyl group; an amino $C_{1-6}$ alkyl group; a $C_{1-6}$ alkyl group substituted with an amidino group; a $C_{1-6}$ alkyl group substituted with a guanidino group; a hydroxy-$C_{1-6}$ alkyl group; a carboxy-substituted $C_{1-6}$ alkyl group, or a $C_{1-6}$ alkyl group substituted with a substituted or non-substituted carbamoyl group. Alternatively, $R^6$ and $R^8$ may combine to form, together with the nitrogen atom to which $R^6$ binds, a 5 or 6-membered nitrogen-containing saturated heterocyclic group having a carboxyl group on its ring. Examples of the heterocyclic group includes 2-carboxy-1-pyrrolidinyl group (-Pro-OH) and 3-carboxy-1-piperidinyl group. Combinations where $R^7$ is a carboxyethyl group or a carbamoylethyl group and $R^8$ is a hydrogen atom are preferred. $R^9$ represents a hydrogen atom or a $C_{1-6}$ alkyl group. In the aforementioned substituents, the alkyl group, alkoxy group, or alkanoyl group may be either straight or branched.

The compounds of the present invention represented by Formula I have an asymmetric carbon atom derived from phenylalanine residue attached to Q, an asymmetric carbon atom substituted with $R^7$ and $R^8$ (except when $R^7$ and $R^8$ simultaneously represent the same substituents), and one or more asymmetric carbon atoms which may optionally exist in each of the above-described substituents, as well as two asymmetric carbon atoms derived from an L-tyrosine residue and D-Arg or L-Arg residues represented by symbol Q. The asymmetric carbon atoms other than those derived from residues of L-Tyr, D-Arg, and L-Arg may have either R- or S-configuration. Any optical isomers or racemates, diastereomers, and mixtures of such isomers fall within the scope of the compounds of the present invention according to Formula I.

Acid addition salts such as hydrochlorides, acetates, or para-toluenesulfonates, or base addition salts such as ammonium salts or organic amine salts also fall within the compounds of the present invention. In addition to the compound represented by the above formula, dimers or oligomers of the above-described compounds and cyclic compounds, in which the C-terminal and N-terminal of these compounds bind, also fall within the compounds of the present invention.

The peptides of the present invention have higher analgesic activity than morphine. Since their analgesic activity is accompanied by weaker effects of the release of histamine and heart rate depression than those of morphine, and since their degree of cross resistance with morphine is low, they can be expected to be suitable for the treatment of cancerous pain. Examples of the route of administration include, for example, intravenous administration, subcutaneous administration, and oral administration. Formulations for mucosal absorption including nasal absorption and formulations for endermic absorption are also expected to be useful.

The peptide derivatives of the present invention can be prepared by solid phase methods and liquid phase methods ordinarily used for peptide preparations. For example, peptide chains may first be prepared without amidino groups by the solid phase method, and then amidino groups may be introduced to the amino group of the N-terminal tyrosine to obtain desired peptide derivatives. Alternatively, amidino groups may be introduced beforehand and the C-terminal can then be modified. Various excellent agents are available as protective groups for amino groups and the like and as condensing agents or the like for condensation reactions. These can be suitably selected with reference to Examples set out below, or in view of, for example, Koichi Suzuki Ed., "Tanpakushitu Kohgaku-Kiso To Ohyo" (Protein Engineering: Fundamentals and Applications), Maruzen Co., Ltd. (1992) and publications cited therein; M. Bodanszky, et al., "Peptide Synthesis", John Wiley & Sons, N.Y., (1976); and J. M. Stewart and D. J. Young, "Solid Phase Peptide Synthesis", W. H. Freeman and Co., San Francisco, 1969. For the solid phase methods, various commercially available peptide synthesizers, for example, Model 430A (Perkin Elmer Japan, formerly Applied Biosystems), may conveniently be used. Resins, reagents and the like used in the preparations are easily obtainable as commercially available products and examples are indicated in the Examples.

EXAMPLES

The present invention will be further explained by way of examples. However, the present invention is not limited to these examples. By referring to the examples, modifying or altering the methods of the present examples, or appropriately selecting starting materials or reagents for reactions, desired peptide derivatives of the present invention that fall within the scope of Formula I can easily be prepared. In the examples, the meanings of amino acid groups are similar to those ordinarily used. Where an amino acid having a D-form and an L-form is referred to, the amino acid represents an L-amino acid unless specifically stated to be a D-form. In addition, the following abbreviations will be used, and similar abbreviations not specifically defined here will occasionally be used.

Example 1

$H_2NC(NH)$-Tyr-D-Arg-Phe-$NHCH_2CH_2COOH$

| Terms used in Examples | Definition |
| --- | --- |
| Z | benzyloxycarbonyl group |
| OTce | trichloroethyl ester group |
| Boc | t-butoxycarbonyl group |
| WSCI | 1-ethyl-3-(3-dimethylaminopropyl)-carbodiimide |
| TsoOH | para-toluenesulfonic acid |
| OBzl | benzyloxy group |
| MeβAla or βMeAla | N-methyl-β-alanine |
| H-βAla-ol | $NH_2CH_2CH_2CH_2OH$ |
| Fmoc | 9-fluorenylmethyloxycarbonyl |
| Pmc | 2,2,5,7,8-pentamethylchroman-6-sulfonyl |
| t-Bu | tertiary-butyl |
| NMP | N-methylpyrrolidone |
| DMF | dimethylformamide |
| DMSO | dimethylsulfoxide |
| TFA | trifluoroacetic acid |
| TEA | triethylamine |
| DCM | dichloromethane |
| DMAP | N,N-dimethylaminopyridine |
| DIPEA | N,N-diisopropylethylamine |
| DIPCI | N,N-diisopropylcarbodiimide |
| HOBt | 1-hydroxybenzotriazole |
| EDC | 1-(3-dimethylaminopropyl)-3-ethyl-carbodiimide |
| HBTU | 2-(1H-benzotriazole-1-yl)-1,1,3,3-tetramethyluronium hexafluorophosphate |
| PyBrop | Bromo tris (pyrrolidino) phosphonium hexafluorophosphate |
| Alko resin | p-alkoxybenzylalcohol resin (4-hydroxymethylphenoxy-methyl-co-polystyrene 1% divinylbenzene resin, J. Am. Chem. Soc., 95, 1328 (1974), Watanabe Chemical Industry) |
| Fmoc-NH-SAL resin | 4-(2',4'-dimethoxyphenyl-9-fluorenylmethoxy-carbonylamionomethyl)phenoxy resin (Watanabe Chemical Industry) |

The above peptide was prepared by the solid phase method (Original Autoprogram for the Fmoc/NMP method) using a Model 430A peptide synthesizer manufactured by Applied Biosystems Inc. (ABI) as follows.

Fmoc-β-Ala-Alko resin (0.25 mmol/675 mg) was washed once with NMP, and treated with NMP containing 20% piperidine for 4 minutes, and then with NMP containing 20% piperidine in the same manner for 16 minutes. The resin was washed with NMP 5 times, and then allowed to react with Fmoc-Phe-OH for 61 minutes. After being washed with NMP 4 times, the resin was recovered from the fourth rinse, and unreacted amino groups were allowed to react with acetic anhydride.

The above-described first cycle was carried out in 120 minutes, and a similar procedure was conducted using Fmoc-D-Arg(Pmc)-OH for Fmoc-Phe-OH in the second cycle, and Fmoc-Tyr(t-Bu)-OH in the third cycle. As side chain protective groups, Pmc was used for D-Arg and t-Bu for Tyr.

500 mg of the resin obtained in the above procedure was treated with stirring in a mixture of phenol (crystal, 0.75 g), ethanedithiol (0.25 ml), thioanisole (0.50 ml), water (0.50 ml) and TFA (10.0 ml) for 3 hours at room temperature to release peptides from the resin and simultaneously remove the protective groups. Then, the mixture was filtered using a 3 µm filter (ADVANTEC-Polyflon filter), cold diethyl ether (200 ml) was added to the filtrate, and the resulting precipitates were collected by filtration using a 3 µm filter (ADVANTEC-Polyflon filter). The precipitates on the filter were dissolved in 10–20 ml of 2N acetic acid and then lyophilized to give crude peptide.

The crude peptide (135 mg) was dissolved in water (13.5 ml), and 1M o-methylisourea (13.5 ml) was added. Stirring was continued for 14 days at 4° C. for amidination. The resulting crude amidinated peptide (106 mg) was dissolved in 20 ml of 0.1% aqueous solution of TFA. After adjustment of pH to 4–5 with 0.01 N hydrochloric acid, the peptide was purified using a Gilson HPLC system. For the HPLC, a Cosmosil $C_{18}$ column was used, and a continuous linear gradient consisting of a mixture of 0.1% aqueous TFA solution and 0.1% aqueous TFA solution containing 70% acetonitrile (mixing ratio was from 0% at time zero to 60% at 45 minutes) was used at the flow rate of 10 ml/minute.

About 100 µg of the purified peptide was applied to a hydrolysis tube and 6 N hydrochloric acid containing 0.2% phenol (1 ml) was added. After evacuation and sealing of the tube, hydrolysis was carried out for 24 hours at 110° C. After cooling to ambient temperature and evaporation to dryness at 40° C., the result was dissolved in 0.01 N hydrochloric acid (1 ml) and 20 µl of the solution was subjected to amino acid analysis using an amino acid analyzer [analyzer: Hitachi L-8500, Column: Hitachi Custom Ion Exchange Resin # 2622, pre-column: Hitachi Custom Ion Exchange Resin # 2650L, buffer: lithium buffer (0.09 N,pH 2.8; 0.25 N,pH 3.7; 0.72 N,pH 3.6; 1.00 N,pH 4.1; regeneration 0.20 N), reaction temperature: 135° C., flow rate of buffer pump: 0.30 ml/minute, flow rate of ninhydrin pump: 0.35 ml/minute, wavelength of detector: 570 nm/440 nm, assay time: 150 minutes]. The result of the amino acid analysis verified the above-mentioned structure.

The purified peptide (about 150 µg) was dissolved in 5% acetic acid (250 µl) and 1 µl of the solution was subjected to mass spectrometric analysis using Liquid SIMS [MS and MS/MS, cesium ion gun was used, analyzer: Finnigan TSQ 700, matrix: glycerol-thioglycerol (1:1), collision gas: Ar gas (3–5 mTorr), collision energy: −20 eV, electron multiplier: 1000 to 1500 V]. The results obtained verified the above-described structure.

Example 2

$H_2NC(NH)$-Tyr-D-Arg-Phe-$NHCH_2CH_2CONH_2$

The above peptide derivative was obtained in the same manner as in Example 1, except that Fmoc-NH-SAL resin (0.25 mmol/385 mg) was used at the beginning of the synthesis, Fmoc-β-Ala-OH in the first cycle, Fmoc-Phe-OH in the second cycle, Fmoc-D-Arg(Pmc)-OH in the third cycle, and Fmoc-Tyr(t-Bu)-OH in the fourth cycle.

Synthesis and purification of the amidinated peptide derivative were also carried out in the same manner as in Example 1 except for use of a mixture of 0.05% aqueous formic acid solution and 0.05% aqueous formic acid solution containing 70% acetonitrile (a continuous linear gradient with a mixing ratio of from 0% at the beginning of HPLC to 40% at 45 minutes). Amino acid analysis and mass spectrometric analysis were also carried out in the same manner as in Example 1, and the results verified the aforementioned structure.

Example 3

$H_2NC(NH)$-Tyr-D-Arg-Phe-$N(CH_3)CH_2CH_2COOH$

The tetrapeptide derivative having the above structure was prepared by the solid phase method according to the Fmoc/NMP method as follows. A glass filter was used for filtration.

After Alko resin (0.500 g) had been swollen with DMF (6 ml), the resin was added with Fmoc-N-methyl-β-alanine (Fmoc-β-MeAla-OH, 0.228 g) and pyridine (0.093 ml), shaken for 1 minute, and then added with 2,6-dichlorobenzoyl chloride (0.147 g) and shaken for 24 hours. The resulting Fmoc-β-MeAla-Alko resin was washed 3 times with 6 ml of DMF, then 3 times with 6 ml of methanol and further 3 times with 6 ml of DCM, and unreacted hydroxymethyl groups were benzoylated by adding benzoyl chloride (0.0891 ml) and pyridine (0.0847 ml) in DCM (6 ml) and shaking for 1 hour. The amino acid resin was successively washed 3 times with 6 ml of DCM, 3 times with 6 ml of DMF and 3 times with 6 ml of methanol and vacuum dried in a desiccator over potassium hydroxide.

The Fmoc-β-MeAla-Alko resin was treated 3 times with 12 ml of DMF, then 3 times with 12 ml of DMF containing 20% piperidine and further 6 times with 12 ml of DMF to remove the Fmoc group, and then added with Fmoc-Phe-OH (0.262 g), PyBrop (Watanabe Chemical Industry, 0.315 g), NMP (6 ml) and DIPEA (0.273 ml) and shaken for 24 hours to form Fmoc-Phe-β-MeAla-Alko resin. After filtration and washing with NMP (6 ml), unreacted amino groups were capped by treatment with DMF (6 ml) containing 1-acetylimidazole (0.248 g) and DIPEA (0.0784 ml) for 1 hour. The resulting resin was then washed with NMP (6 ml).

The Fmoc group was removed from the Fmoc-Phe-β-MeAla-Alko resin in the same manner as described above, and the result was added with Fmoc-D-Arg(Pmc)-OH (0.557 g), HOBt (0.121 g), HBTU (0.299 g) and DIPEA (0.274 ml) and shaken for 1 hour to form Fmoc-D-Arg(Pmc)-Phe-β-MeAla-Alko resin. Subsequently, after filtration and washing, unreacted amino groups were capped in the same manner as described above.

The Fmoc group was removed from the Fmoc-D-Arg(Pmc)-Phe-β-MeAla-Alko resin obtained in the same manner as described above, and the result was added with Fmoc-Tyr(t-Bu)-OH (0.310 g), HOBt (0.103 g), HBTU (0.256 g) and DIPEA (0.235 ml) and shaken for 1 hour to form Fmoc-Tyr(t-Bu)-D-Arg(Pmc)-Phe-β-MeAla-Alko resin. After filtration and washing in the same manner as described above, unreacted amino groups were capped.

The Fmoc group was removed from the Fmoc-Tyr(t-Bu)-D-Arg(Pmc)-Phe-β-MeAla-Alko resin in the same manner as described above, and the result was added with 1H-pyrazole-1-carboxyamidine hydrochloride (0.989 g) prepared according to the method of Matsueda et al. (The Journal of Organic Chemistry, 57, 2497–2502, 1992), DIPEA (1.293 ml) and DMF (6 ml), and allowed to react at from 10 to 60° C., more preferably, at from 40 to 500C, for from 1 to 4 hours to amidinate the amino group of the N-terminal tyrosine. Then, the result was filtered, washed (3 times with 6 ml of NMP and further 3 times with 6 ml of methanol) and vacuum dried in a desiccator over potassium hydroxide.

The resin (596 mg) obtained by the above procedure was placed on a glass filter and treated with a mixture of TFA, phenol and water (5 ml, TFA:phenol:water=93:2:5) for 1 hour and filtered. The same treatment was repeated twice. The resin was further treated with TFA (5 ml) for 5 minutes and filtered. The same treatment was repeated 3 times. The filtrates obtained by the treatments were combined and the solvent was removed under reduced pressure at a temperature below 20° C. After repeating a treatment in which residue was added with diethyl ether (20 ml) to form white precipitates and the supernatant was discarded, the resulting white powder was dissolved in water (20 ml), washed with diethyl ether (5 ml) 3 times in a separation funnel, and the aqueous layer was lyophilized to obtain crude amidino peptide.

The crude amidino peptide (56.2 mg) was dissolved in a 0.05% aqueous TFA solution (10 ml) and purified by a Shimazu HPLC system. For the HPLC, a YMC D-ODS-5-ST $C_{18}$ column and a mixture of 0.05% aqueous TFA solution containing 0.5% acetonitrile and 0.05% aqueous TFA solution containing 70% acetonitrile (a linear gradient at a mixing ratio of from 0% at the beginning of HPLC to 90% at 50 minutes at the flow rate of 1 ml/minute) were used. Amino acid analysis and mass spectrometric analysis were carried out in the same manner as in Example 1. The results verified the above structure.

Example 4

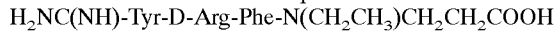

$H_2NC(NH)$-Tyr-D-Arg-Phe-$N(CH_2CH_3)CH_2CH_2COOH$

The tetrapeptide derivative having the above structure was prepared by the solid phase method according to the Fmoc/NMP method as follows. A glass filter was used for filtration.

After Alko resin (1.000 g) had been swollen with DMF (12 ml), the resin was added with Fmoc-N-ethyl-β-alanine (Fmoc-β-EtAla-OH, 0.475 g) and DMAP (0.017 g), shaken for 1 minute, then added with DIPCI (0.177 g) and shaken for 24 hours. The resulting Fmoc-β-EtAla-Alko resin was washed 3 times with 12 ml of NMP, then 3 times with 12 ml of methanol and further 3 times with 12 ml of DCM, and unreacted hydroxymethyl groups were benzoylated by adding benzoyl chloride (0.178 ml) and pyridine (0.170 ml) in DCM (12 ml) and shaking for 1 hour. Then, the amino acid resin was successively washed 3 times with 12 ml of DCM, 3 times with 12 ml of DMF, and 3 times with 12 ml of methanol and vacuum dried in a desiccator over potassium hydroxide.

The Fmoc-β-EtAla-Alko resin was treated 3 times with 20 ml of DMF, then 3 times with 12 ml of DMF containing 20% piperidine and further 6 times with 12 ml of DMF to remove the Fmoc groups, and added with Fmoc-Phe-OH (0.387 g), PyBrop (0.466 g), NMP (12 ml) and DIPEA (0.523 ml) and shaken for 24 hours to afford Fmoc-Phe-β-EtAla-Alko resin. After filtration, the result was washed with NMP (12 ml) and unreacted amino groups were capped by treatment with DMF (12 ml) containing 1-acetylimidazole (0.551 g) and DIPEA (0.174 ml) for 1 hour. Then, the resulting resin was again washed with NMP (12 ml).

The Fmoc group was removed from the Fmoc-Phe-β-EtAla-Alko resin obtained above in the same manner as described above. The resin was added with Fmoc-D-Arg (Pmc)-OH (0.707 g), HOBt (0.153 g), HBTU (0.379 g) and DIPEA (0.348 ml) and shaken for 1 hour to obtain Fmoc-D-Arg(Pmc)-Phe-β-EtAla-Alko resin. Unreacted amino groups were capped after filtration and washing in the same manner as described above.

The Fmoc group was removed from the Fmoc-D-Arg (Pmc)-Phe-β-EtAla-Alko resin in the same manner as described above. The resin was added with Fmoc-Tyr(t-Bu)-OH (0.460 g), HOBt (0.153 g), HBTU (0.399 g) and DIPEA (0.348 ml) and shaken for 1 hour to form Fmoc-Tyr(t-Bu)-D-Arg(Pmc)-Phe-β-EtAla-Alko resin. After filtration and washing, unreacted amino groups were capped in the same manner as described above.

The Fmoc group was removed from the Fmoc-Tyr(t-Bu)-D-Arg(Pmc)-Phe-β-EtAla-Alko resin in the same manner as described above. The resin was added with 1-H-pyrazole-1-carboxyamidine hydrochloride (2.199 g) prepared in the same manner as in Example 3, DIPEA (2.874 ml) and DMF (6 ml) and allowed to react at 40 to 50° C. for 1 to 4 hours for the amidination of amino groups at N-terminal tyrosine. Then, the result was filtered, washed (3 times with 12 ml of NMP and further 3 times with 12 ml of methanol) and vacuum dried in a desiccator over potassium hydroxide.

The resin (1.514 g) obtained by the procedure described above was placed on a glass filter and treated with 10 ml of a mixture containing TFA, phenol, and water (TFA:phenol:water=93:2:5) for 1 hour and filtered. The same treatment was repeated twice. The resin was further treated with TFA (10 ml) for 5 minutes and filtered. The same treatment was repeated 3 times. The filtrates obtained from the treatments were combined and the solvent was removed under reduced pressure at a temperature below 20° C. A treatment in which the residue was added with diethyl ether (20 ml) to form white precipitates and the supernatant was discarded was repeated 3 times. The resulting white powder was dissolved in water (30 ml), washed with 5 ml of diethyl ether 3 times in a separation funnel and the aqueous layer was lyophilized to obtain crude amidino peptide.

The crude amidino peptide (100 mg) was dissolved in a 0.05% aqueous TFA solution (20 ml) and purified in the same manner as in Example 3. Amino acid analysis and mass spectrometric analysis were carried out in the same manner as in Example 1. The results verified the above-described structure.

Example 5

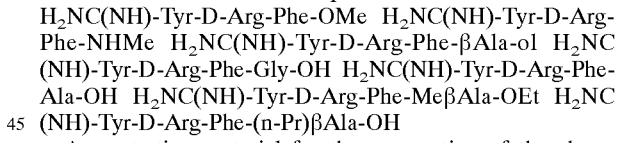

$H_2NC(NH)$-Tyr-D-Arg-Phe-OMe $H_2NC(NH)$-Tyr-D-Arg-Phe-NHMe $H_2NC(NH)$-Tyr-D-Arg-Phe-βAla-ol $H_2NC(NH)$-Tyr-D-Arg-Phe-Gly-OH $H_2NC(NH)$-Tyr-D-Arg-Phe-Ala-OH $H_2NC(NH)$-Tyr-D-Arg-Phe-MeβAla-OEt $H_2NC(NH)$-Tyr-D-Arg-Phe-(n-Pr)βAla-OH

As a starting material for the preparation of the above peptides, the protected peptide represented by the formula Z-HNC(N-Z)-Tyr(Bzl)-D-Arg($Z_2$)-Phe-OH was prepared by a liquid method as follows:

The starting material, Z-Phe-OTce (254 g), was treated with 25% hydrogen bromide-acetic acid (900 ml) to remove the Z group and then dissolved in $CH_2Cl_2$ (1000 ml) on an ice bath. After this solution was added with Boc-D-Arg($Z_2$)-OH (288 g) and HOBt (85 g) and neutralized with TEA (77 ml), a condensation reaction was carried out by using EDC.HCl (121 g) to form Boc-D-Arg($Z_2$)-Phe-OTce. Then, Boc-D-Arg($Z_2$)-Phe-OTce (241 g) was treated with 4N HCl-ethyl acetate (1000 ml) to remove the Boc group and dissolved in DMF (1300 ml) on an ice bath. After the solution was added with Boc-Tyr(Bzl)-OH (108 g) and HOBt (46 g) and neutralized with TEA (42 ml), condensation reaction was carried out using ED.HCl (65 g) to obtain a protected peptide of the formula Boc-Tyr(Bzl)-D-Arg($Z_2$)-Phe-OTce.

The Boc-Tyr(Bzl)-D-Arg($Z_2$)-Phe-OTce (48 g) was treated with 4N HCl-ethyl acetate (250 ml) to remove Boc group and then dissolved in DMF (150 ml) on an ice bath.

The solution was neutralized with TEA (7 ml) and added with Z-HNC(N-Z)-pyrazole (amidination reagent, 19 g) and stirred at room temperature to obtain the protected peptide Z-HNC(N-Z)-Tyr(Bzl)-D-Arg(Z$_2$)-Phe-OTce. This protected peptide (42 g) was dissolved in acetic acid on a water bath, added with zinc powder (21 g, 0.32 ml) and stirred for 2 hours. After the zinc powder was removed from the reaction mixture, concentration under reduced pressure gave the protected peptide Z-HNC(N-Z)-Tyr(Bzl)-D-Arg (Z$_2$)-Phe-OH.

The Z-HNC(N-Z)-Tyr(Bzl)-D-Arg(Z$_2$)-Phe-OH was condensed with MeOH (EDC-DMAP method); NH$_2$Me (EDC-HOBt method); H-βAla-ol(EDC-HOBt method); H-Gly-OBzl.TosOH (EDC-HOBt method); H-Ala-OBzl.TosOH (EDC-HOBt); H-MeβAla-OEt (EDC-HOBt method); or H-(n-Pr)βAla-OBzl.TosOH (EDC-HOBt method). Each of the resulting products was dissolved in acetic acid on a water bath and subjected to catalytic hydrogenation in the presence of palladium on carbon. The catalyst was removed and the reaction mixture was concentrated under reduced pressure and subsequently lyophilized to give the desired peptides in the form of powder. The results of amino acid analysis and mass spectrometric analysis under the conditions set out below verified the structure of each resulting peptide.

For the amino acid analysis, the peptide (approximately 0.5 mg) was placed in a hydrolysis tube and added with 6N hydrochloric acid (1 ml). After evacuation and sealing of the tube, hydrolysis was carried out for 24 hours at 110° C. After cooling to ambient temperature, the result was concentrated to dryness at 40° C., and then the residue was dissolved in purified water (5 ml). A portion (5 μl) was sampled from the solution and dried under reduced pressure, and then the residue was added with 20 μl of 50 mM NaHCO$_3$ buffer (pH 9.0) and 40 μl of dabsyl chloride-acetonitrile solution and warmed at 70° C. for 10 minutes. The reaction mixture was concentrated under reduced pressure and the residue was dissolved in 50% ethanol (100 μl). The resulting solution (20 μl) was analyzed by liquid chromatography. For the mass spectrometric analysis, about 150 μg of the peptide was dissolved in 5% acetic acid (250 μl) and a portion (1 μl) was analyzed by Liquid SIMS.

Example 6

H$_2$NC(NH)-Tyr-D-Arg-MePhe-MeβAla-OH H$_2$NC(NH)-Tyr-D-Arg-EtPhe-MeβAla-OH

The above peptides were prepared successively from the C-terminals by a liquid method using TosOH.MeβAla-OBzl as a starting material. Boc-MePhe-OH and TosOH.MeβAla-OBzl were condensed by the EDC-HOBt method to afford Boc-MePhe-MeβAla-OBzl. The Boc group was removed from the Boc-MePhe-Meβla-OBzl using 4N HCl-ethyl acetate, and the result was condensed with Boc-D-Arg(Z$_2$)-OH by the EDC-HOBt method to form Boc-D-Arg(Z$_2$)-MePhe-MeβAla-OBzl. Subsequently, Boc group was removed from the Boc-D-Arg(Z$_2$)-MePhe-MeβAla-OBzl using 4 N HCl-ethyl acetate, and the result was condensed with Boc-Tyr(Bzl)-OH by EDC-HOBt method to obtain the protected peptide Boc-Tyr(Bzl)-D-Arg(Z$_2$)-MePhe-MeβAla-OBzl.

The Boc-Tyr(Bzl)-D-Arg(Z$_2$)-MePhe-MeβAla-OBzl was treated with 4N HCl-ethyl acetate to remove Boc group, and then the protected peptide Z-HNC(N-Z)-Tyr(Bzl)-D-Arg (Z$_2$)-MePhe-MeβAla-OBzl was obtained by adding Z-HNC (N-Z)-pyrazole (amidination reagent) and stirring at room temperature. This protected peptide was dissolved in acetic acid. After addition of palladium on carbon, catalytic hydrogenation was carried out by bubbling hydrogen gas into the solution. After the palladium on carbon was removed, concentration under reduced pressure and lyophilization gave the peptide H$_2$NC(NH)-Tyr-D-Arg-MePhe-MeβAla-OH in the form of powder. By the amino acid analysis and mass spectrometric analysis described in Example 5, the peptide was verified to have the above structure.

By using Boc-EtPhe-OH instead of Boc-MePhe-OH, Boc-EtPhe-MeβAla-OBzl was prepared by condensation with TosOH.MeβAla-OBzl by the EDC-HOBt method in a similar manner to those described above. Then, deprotection and condensation were repeated in the same manner as described above to give the protected peptide Z-HNC(N-Z)-Tyr(Bzl)-D-Arg(Z$_2$)-EtPhe-MeβAla-OBzl. This protected peptide was dissolved in acetic acid and added with palladium on carbon. Catalytic hydrogenation was carried out by bubbling hydrogen gas into the solution. After the palladium on carbon was removed, concentration under reduced pressue and lyophilization gave the peptide H$_2$NC (NH)-Tyr-D-Arg-EtPhe-MeβAla-OH in the form of a powder. By the amino acid analysis and mass spectrometric analysis described in Example 5, the peptide was verified to have the above structure.

Example 7

H$_2$NC(NH)-Tyr-D-Arg-Phe-MeβAla-OH

Preparation was carried out according to a liquid phase method ordinary used for peptide synthesis. Z-Phe-OTce (254 g), used as a starting material, was treated with 25% hydrogen bromide-acetic acid (900 ml) to remove the Z group and dissolved in CH$_2$Cl$_2$ (1000 ml) on an ice bath. This solution was added with Boc-D-Arg(Z$_2$)-OH (288 g) and HOBt (85 g) and neutralized with TEA (77 ml), and then condensed with EDC.HCl (121 g) to obtain Boc-D-Arg (Z$_2$)-Phe-OTce. Subsequently, the Boc-D-Arg(Z$_2$)-Phe-OTce (241 g) was treated with 4N HCl-ethyl acetate (1000 ml) to remove Boc group and then dissolved in DMF (1300 ml) on an ice bath. The solution was added with Boc-Tyr (Bzl)-OH (108 g) and HOBt (46 g) and neutralized with TEA (42 ml), and then condensation was carried out using EDC.HCl (65 g) to obtain a protected peptide represented by the formula Boc-Tyr(Bzl)-D-Arg(Z$_2$)-Phe-OTce.

The Boc-Tyr(Bzl)-D-Arg(Z$_2$)-Phe-OTce (48 g) was treated with 4N HCl-ethyl acetate (250 ml) to remove Boc group and dissolved in DMF (150 ml) on an ice bath. The solution was neutralized with TEA (7 ml) and added with Z-HNC(N-Z)-pyrazole (amidination reagent, 19 g) and stirred at room temperature to give the protected peptide of the formula Z-HNC(N-Z)-Tyr(Bzl)-D-Arg(Z$_2$)-Phe-OTce. This protected peptide (42 g) was dissolved in acetic acid on a water bath, added with zinc powder (21 g), and then stirred for 2 hours. After the zinc powder was removed from the reaction mixture, concentration under reduced pressure gave the protected peptide Z-HNC(N-Z)-Tyr(Bzl)-D-Arg(Z$_2$)-Phe-OH.

This protected peptide Z-HNC(N-Z)-Tyr(Bzl)-D-Arg (Z$_2$)-Phe-OH (1.15 g) and TosOH.MeβAla-OBzl (0.93 g) were dissolved in 30 ml of DMF (containing 10% DMSO) on an ice bath. This solution was added with HOBt (0.24 g) and neutralized with TEA (0.21 ml), and then condensation was carried out using EDC.HCl (0.25 g) to obtain the protected peptide represented by the formula Z-HNC(N-Z)-Tyr(Bzl)-D-Arg(Z$_2$)-Phe-MeβAla-OBzl. The protected peptide (0.90 g) was dissolved in acetic acid (100 ml) and added with palladium on carbon. Catalytic hydrogenation was carried out by bubbling hydrogen gas into the solution. After palladium on carbon was removed, concentration under reduced pressure and lyophilization gave the peptide H$_2$NC (NH)-Tyr-D-Arg-Phe-MeβAla-OH in the form of a powder. By the amino acid analysis and mass spectrometric analysis described in Example 5, the peptide was verified to have the above structure.

As physicochemical properties of the peptide derivatives of the present invention, HPLC retention times and Rf values of thin layer chromatography are shown in Table 1. All of these peptide derivatives were obtained as lyophilized products. Conditions for HPLC:

| Conditions for HPLC: | |
|---|---|
| Apparatus: | Nihon-Bunkou 880 System |
| Column: | Nucleosil 5C18 100A |
| Solvent: | Solution A |
| | (acetonitrile:purified water:trifluoro acetic acid=10:90:0.1) |
| | Solution B |
| | (acetonitrile:purified water:trifluoro acetic acid=70:30:0.1) |
| Gradient: | Solution B 0–100%/30 min. |
| Flow Rate: | 1 ml/min. |
| Temperature: | 40° C. |
| Wavelength for detection: | 230 nm |
| Injection Volume: | 20 μl of sample (conc. 1 mg/ml) was injected by an automatic sample injector |
| Conditions for thin layer chromatography: | |
| $Rf^a$: | n-butanol:acetic acid:purified water=4:1:5 was mixed and then the supernatant was used as developing solution. |
| $Rf^b$: | n-butanol:acetic acid:purified water: pyridine=15:3:10:12 was used as developing solution. |
| Thin layer plate: | Silica gel (Merck F254) |

Other compounds obtained in the same manner as in the aforementioned examples are shown in Table 2.

TABLE 1

| Peptide derivatives of the Present Invention | HPLC (Retention Time) | $Rf^a$ | $Rf^b$ |
|---|---|---|---|
| 1. H$_2$NC(NH)-Tyr-D-Arg-Phe-NH(CH$_2$)$_2$COOMe | 10.79 | 0.49 | 0.74 |
| 2. H$_2$NC(NH)-Tyr-D-Arg-Phe-N(CH$_3$)(CH$_2$)$_2$COOMe | 12.22 | 0.47 | 0.74 |
| 3. H$_2$NC(NH)-Tyr-D-Arg-Phe-OMe | 11.37 | 0.60 | 0.84 |
| 4. H$_2$NC(NH)-Tyr-D-Arg-Phe-NHCH(CH$_3$)CH$_2$OH | 9.11 | 0.46 | 0.70 |
| 5. H$_2$NC(NH)-Tyr-D-Arg-Phe-Arg-NH$_2$ | 7.83 | 0.23 | 0.55 |
| 6. H$_2$NC(NH)-Tyr-D-Arg-Phe-Leu-OH | 13.19 | 0.41 | 0.64 |
| 7. H$_2$NC(NH)-Tyr-D-Arg-Phe-OH | 9.35 | 0.50 | 0.76 |
| 8. H$_2$NC(NH)-Tyr-D-Arg-Phe-Gly-OH | 8.54 | 0.37 | 0.60 |
| 9. H$_2$NC(NH)-Tyr-D-Arg-Phe-Asp-OH | 8.41 | 0.25 | 0.44 |
| 10. H$_2$NC(NH)-Tyr-D-Arg-Phe-Ala-OH | 9.27 | 0.43 | 0.66 |
| 11. H$_2$NC(NH)-Tyr-D-Arg-Phe-N(CH$_3$)CH$_2$CH$_2$OH | 9.64 | 0.51 | 0.74 |
| 12. H$_2$NC(NH)-Tyr-D-Arg-Phe-N(CH$_3$)CH$_2$COOMe | 11.49 | 0.49 | 0.74 |
| 13. H$_2$NC(NH)-Tyr-D-Arg-Phe-Gly-NH$_2$ | 8.09 | 0.38 | 0.60 |
| 14. H$_2$NC(NH)-Tyr-D-Arg-Phe-N(CH$_3$)(CH$_2$)$_2$CON(Me)$_2$ | 11.11 | 0.35 | 0.69 |
| 15. H$_2$NC(NH)-Tyr-D-Arg-Phe-Pro-OH | 10.68 | 0.33 | 0.54 |
| 16. H$_2$NC(NH)-Tyr-D-Arg-Phe-NHMe | 9.01 | 0.43 | 0.68 |
| H$_2$NC(NH)-Tyr-D-Arg-Phe-N(CH$_3$)(CH$_2$)$_2$CONH(n-Hex) | 17.26 | 0.52 | 0.79 |
| 17. H$_2$NC(NH)-Tyr-D-Arg-Phe-NHEt | 10.24 | 0.59 | 0.81 |
| 18. H$_2$NC(NH)-Tyr-D-Arg-Phe-D-Ala-NH$_2$ | 9.09 | 0.40 | 0.67 |
| 19. H$_2$NC(NH)-Tyr-D-Arg-Phe-N(CH$_3$)CH(CH$_3$)COOH | 10.81 | 0.42 | 0.67 |
| 20. H$_2$NC(NH)-Tyr-D-Arg-D-Phe-N(CH$_3$)CH(CH$_3$)COOH | 11.58 | 0.41 | 0.58 |
| 21. H$_2$NC(NH)-Tyr-D-Arg-Phe-NHC(CH$_3$)$_2$COOH | 10.57 | 0.41 | 0.61 |
| 22. H$_2$NC(NH)-Tyr-D-Arg-Phe-(R)-NHCH(C$_2$H$_5$)COOH | 11.17 | 0.39 | 0.59 |
| 23. H$_2$NC(NH)-Tyr-D-Arg-Phe-D-Ala-OH | 9.94 | 0.40 | 0.65 |
| 24. H$_2$NC(NH)-Tyr-Arg-Phe-N(CH$_3$)(CH$_2$)$_2$COOH | 11.65 | 0.33 | 0.54 |
| 25. H$_2$NC(NH)-Tyr-D-Arg-Phe-NHCH$_2$CH$_2$SO$_3$H | 7.67 | 0.38 | 0.68 |
| 26. 1-[H$_2$NC(NH)-Tyr-D-Arg-Phe]-piperidine | 14.87 | 0.66 | 0.80 |
| 27. 1-[H$_2$NC(NH)-Tyr-D-Arg-Phe]-piperazine | 7.55 | 0.28 | 0.60 |
| 28. H$_2$NC(NH)-Tyr-D-Arg-Phe-N(CH$_2$C$_6$H$_5$)(CH$_2$)$_2$COOH | 14.87 | 0.51 | 0.70 |
| 29. H$_2$NC(NH)-Tyr-D-Arg-Phe-(R,S)-NHCH$_2$CH(CH$_3$)COOH | 9.96 | 0.47 | 0.62 |
| 30. H$_2$NC(NH)-Tyr-D-Arg-Phe-N(CH$_2$CH$_3$)(CH$_2$)$_2$COOMe | 12.74 | 0.47 | 0.74 |
| 31. H$_2$NC(NH)-Tyr-D-Arg-Phe-Phe-OH | 13.86 | 0.41 | 0.62 |

TABLE 2

| Peptide Derivatives of the Present Invention | |
|---|---|
| No. | Structure |
| 32. | Et-HNC(NH)-Tyr-(D)Arg-Phe-MeβAla-OH |
| 33. | Et-HNC(NH)-Tyr-(D)Arg-Phe-βAla-OH |
| 34. | n-Pr-HNC(NH)-Tyr-(D)Arg-Phe-βAla-OH |
| 35. | Ph-HNC(NH)-Tyr-(D)Arg-Phe-βAla-OH |
| 36. | Ac-HNC(NH)-Tyr-(D)Arg-Phe-βAla-OH |
| 37. | H$_2$NC(NH)-Tyr-(D)Arg-Phe-NH(n-Pr) |
| 38. | H$_2$NC(NH)-Tyr-(D)Arg-Phe-NH(CH$_2$)$_2$OH |
| 39. | H$_2$NC(NH)-Tyr-(D)Arg-Phe-NHCH(CH$_3$)CH$_2$OH[D] |
| 40. | H$_2$NC(NH)-Tyr-(D)Arg-Phe-NH(CH$_2$)$_3$OH |
| 41. | H$_2$NC(NH)-Tyr-(D)Arg-Phe-NH(CH$_2$)$_4$OH |
| 42. | H$_2$NC(NH)-Tyr-(D)Arg-Phe-Gly-OMe |
| 43. | H$_2$NC(NH)-Tyr-(D)Arg-Phe-Gly-NHMe |
| 44. | H$_2$NC(NH)-Tyr-(D)Arg-Phe-MeGly-OH |
| 45. | H$_2$NC(NH)-Tyr-(D)Arg-Phe-Ala-OMe |
| 46. | H$_2$NC(NH)-Tyr-(D)Arg-Phe-Ala-NH$_2$ |
| 47. | H$_2$NC(NH)-Tyr-(D)Arg-Phe-Ala-NHMe |
| 48. | H$_2$NC(NH)-Tyr-(D)Arg-Phe-(D)Ala-NHMe |
| 49. | H$_2$NC(NH)-Tyr-(D)Arg-Phe-(D)MeAla-OH |
| 50. | H$_2$NC(NH)-Tyr-(D)Arg-Phe-βAla-OH |
| 51. | H$_2$NC(NH)-Tyr-(D)Arg-Phe-MeβAla-OH |
| 52. | H$_2$NC(NH)-Tyr-(D)Arg-Phe-MeβAla-NH$_2$ |
| 53. | H$_2$NC(NH)-Tyr-(D)Arg-Phe-MeβAla-NHMe |
| 54. | H$_2$NC(NH)-Tyr-(D)Arg-Phe-MeβAla-NHEt |
| 55. | H$_2$NC(NH)-Tyr-(D)Arg-Phe-MeβAla-NH(n-Pr) |
| 56. | H$_2$NC(NH)-Tyr-(D)Arg-Phe-MeβAla-N(Et)$_2$ |
| 57. | H$_2$NC(NH)-Tyr-(D)Arg-Phe-EtβAla-OMe |
| 57. | H$_2$NC(NH)-Tyr-(D)Arg-Phe-(D)Arg-NH$_2$ |
| 58. | H$_2$NC(NH)-Tyr-(D)Arg-Phe-Asu-OH |
| 59. | H$_2$NC(NH)-Tyr-(D)Arg-Phe-Sar-OH |
| 60. | H$_2$NC(NH)-Tyr-(D)Arg-Phe-Pro-OH |
| 61. | H$_2$NC(NH)-Tyr-(D)Arg-Phe-Pro-OMe |

Experiments

The analgesic activities of the peptide derivatives of the present invention were evaluated by the pressure stimulation method using one of two devices. In method A, analgesy meter Model 7,200 manufactured by UGO BASILE (Comerio, Italy) was used (units of tail pressure expressed in grams). In method B, an apparatus made by inventor Professor S. Sakurada was used (units of tail pressure expressed in mmHg). Mice were subjected to pressure stimulation at the bases of their tails at a given rate(Method A: 32 g/s; Method B: 10 mmHg/second). Pressure values where mice showed behaviors such as writhing and biting at the stimulated site were measured, and were used as pain reaction thresholds. For the experiments, mice that normally responded to a given pressure of 100–200 g (Method A) or 40–50 mmHg (Method B) were used. The maximum stimulating pressure was 500 g (Method A) or 100 mmHg (Method B). Analgesic activity was calculated as percent of maximum possible effect (% of MPE) according to the equation:

$$\% \text{ of } MPE = \frac{Pt - Po}{Pc - Po} \times 100$$

Wherein Po is the pain reaction threshold before the administration of a drug; Pt is the pain reaction threshold "t" minutes after the administration of the drug; and Pc is the maximum stimulating pressure. $ED_{50}$ values were calculated based on dose response curves as doses that induced 50 percent of % of MPE and analgesic activities of the drugs were compared. The results obtained from subcutaneous administration (s.c.; skin on the backs of the mice was used) and oral administration (p.o.)are shown in Table 3.

TABLE 3

| Test Sample | Method A $ED_{50}$ (mg/kg) | | Method B $ED_{50}$ (mg/kg) | |
|---|---|---|---|---|
| | s.c. | p.o. | s.c. | p.o. |
| Control (morphine) | 3.3 | 22.2 | 4.6 | 29.6 |

TABLE 3-continued

| Test Sample | Method A $ED_{50}$ (mg/kg) | | Method B $ED_{50}$ (mg/kg) | |
|---|---|---|---|---|
| | s.c. | p.o. | s.c. | p.o. |
| $H_2NC(NH)$-Tyr-D-Arg-Phe-$NHCH_2CH_2COOH$ | 0.32 | 18.5 | 0.14 | 5.8 |
| $H_2NC(NH)$-Tyr-D-Arg-Phe-$NHCH_2CH_2CONH_2$ | NT* | NT | 0.13 | 10.7 |
| $H_2NC(NH)$-Tyr-D-Arg-Phe-$N(CH_3)CH_2CH_2COOH$ | 0.09 | 5.8 | 0.10 | 6.6 |
| $H_2NC(NH)$-Tyr-D-Arg-Phe-$N(CH_2CH_3)CH_2CH_2COOH$ | NT | NT | 0.15 | 16.0 |
| $H_2NC(NH)$-Tyr-(D)Arg-Phe-$N(Me)_2$ | NT | NT | 1.22 | NT |
| $H_2NC(NH)$-Tyr-(D)Arg-Phe-$N(CH_3)CH_2CONH_2$ | NT | NT | 0.27 | NT |
| $H_2NC(NH)$-Tyr-D-Arg-Phe-$N(CH_3)CH_2COOH$ | 0.39 | 17.8 | 0.13 | 4.9 |
| $H_2NC(NH)$-Tyr-D-Arg-Phe-$NHCH_2CH_2OH$ | NT | NT | 0.88 | NT |
| $H_2NC(NH)$-Tyr-D-Arg-Phe-$N(CH_3)CH_2CH_2CONH$ | 0.31 | 24.6 | NT | NT |
| $H_2NC(NH)$-Tyr-D-Arg-Phe-$N(CH_3)CH_2CH_2COOCH_3$ | 0.12 | 8.9 | NT | NT |
| 1-[$H_2NC(NH)$-Tyr-D-Arg-Phe]-piperidine-3-COOH | 0.25 | NT | NT | NT |

*NT= Not Taken.

Industrial Applicability

The peptide derivatives of the present invention are useful since they can be used for the treatment of cancerous pain.

What is claimed is:

1. The compound $H_2NC(NH)$-Tyr-D-Arg-Phe-$N(CH_3)CH_2CH_2COOH$ or a salt thereof.

* * * * *